(12) United States Patent
Burkhardt et al.

(10) Patent No.: US 6,624,248 B2
(45) Date of Patent: *Sep. 23, 2003

(54) POLYMERIC DIPHOSPHINE LIGANDS FOR HOMOGENEOUSLY SOLUBLE HYDROGENATION CATALYSTS, PROCESS FOR THE PRODUCTION THEREOF AND USE

(75) Inventors: Olaf Burkhardt, Kalmthout (BE); Jens Woltinger, Hanau (DE); Andreas Bommarius, Atlanta, GA (US); Juan Jose Almena Perea, Hanau (DE); Hans Henniges, Bonn (DE); Karlheinz Drauz, Freigericht (DE); Andreas Karau, Neustadt (DE); Jean-Louis Philippe, Dreieich (DE); Hans-Peter Krimmer, Dietzenbach (DE); Gunther Oehme, Rostock (DE)

(73) Assignee: Degussa AG, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/767,873

(22) Filed: Jan. 24, 2001

(65) Prior Publication Data

US 2001/0034417 A1 Oct. 25, 2001

(30) Foreign Application Priority Data

Jan. 24, 2000 (DE) .......................................... 100 02 973

(51) Int. Cl.$^7$ ............................................... C08L 85/02
(52) U.S. Cl. ...................... 525/102; 502/158; 502/159; 502/162; 525/123; 525/130; 525/188; 528/30; 528/72
(58) Field of Search ..................... 528/30, 72; 525/102, 525/130, 123, 188; 502/158, 159, 162

(56) References Cited

U.S. PATENT DOCUMENTS

| 4,424,312 | A | | 1/1984 | Stille |
| 4,634,775 | A | | 1/1987 | Beck et al. |
| 4,879,389 | A | | 11/1989 | Achiwa |
| 4,923,996 | A | * | 5/1990 | Muller et al. ................ 548/402 |
| 5,306,853 | A | * | 4/1994 | Pugin et al. ................ 585/269 |
| 5,777,062 | A | * | 7/1998 | Pugin |
| 5,990,318 | A | * | 11/1999 | Chan et al. .................. 548/412 |
| 6,284,925 | B1 | | 9/2001 | Knochel et al. |
| 6,348,620 | B1 | | 2/2002 | Knochel et al. |

FOREIGN PATENT DOCUMENTS

| DE | 196 47 892 | 6/1998 |
| DE | 199 21 924 | 12/1999 |
| DE | 199 56 374 | 6/2000 |
| EP | 0 336 123 | 10/1989 |
| EP | 0 965 574 | 12/1999 |
| JP | 2000-053593 | 2/2000 |
| JP | 2000-143684 | 5/2000 |

OTHER PUBLICATIONS

English Abstract EP 965 574 Dec. 1999.
English Abstract DE 1 9921924 Dec. 1999.
English Abstract JP 2000–053593 Feb. 2000.
English Abstract JP 2000—143684 May 2000.
English Abstract DE 199 56 374 6/00.

* cited by examiner

*Primary Examiner*—Margaret G. Moore
(74) *Attorney, Agent, or Firm*—Oblon, Spivak, McClelland, Maier & Neustadt P.C.

(57) ABSTRACT

Molecular weight-enlarged, homogeneously soluble ligands are provided that are especially useful for hydrogenation catalysts, wherein the ligands contain homochiral active centers of bis(3,4-diarylphosphinyl)pyrrolidines, and their use in producing cataylsts for enantioselective reactions, as well as the catalysts thus produced.

10 Claims, No Drawings

POLYMERIC DIPHOSPHINE LIGANDS FOR HOMOGENEOUSLY SOLUBLE HYDROGENATION CATALYSTS, PROCESS FOR THE PRODUCTION THEREOF AND USE

BACKGROUND OF THE INVENTION

1. Field of the Invention

The present invention relates to molecular weight-enlarged ligands for catalysts for the asymmetric, homogeneous hydrogenation of double bonds.

2. Discussion of the Background

Catalytically active species for asymmetric, homogenous hydrogenation of double bonds are extremely advantageous for the industrial synthesis of organic substances. This is particularly the case due to their improved recyclability, which helps keep manufacturing costs low.

Molecular weight-enlarged catalysts for homogeneous enantioselective hydrogenation have been previously disclosed. J. Am. Chem. Soc. 1998, 120, 9481 et seq. addresses the problem of producing soluble molecular weight enlargements, inter alia for hydrogenation catalysts. Wandrey et al. have also reported the use of a molecular weight-enlarged hydrogenation catalyst in a membrane reactor (Angew. Chem. 1990, 102, 445 et seq.). U.S. Pat. No. 5,777,062 describes homogeneously soluble polymer-enlarged ligands for hydrogenation catalysts. The monomeric ligands are bound in that case to the polymer backbone through urethane or urea linkers.

The problems associated with the use of such catalysts have not been previously adequately resolved. Accordingly, there is still a need for novel catalyst systems which make it possible to perform continuous processes catalytically. The problems that must be addressed relate, for example, to the separability of the product from the catalyst with regard to the membrane used and to inactivation of the catalyst over time.

SUMMARY OF THE INVENTION

Accordingly, one object of the present invention is to provide a homogenous soluble hydrogenation catalyst that is readily separable from the product of hydrogenation.

A further object of the present invention is to provide a homogenous soluble hydrogenation catalyst having improved lifetime.

A further object of the present invention is to provide a molecular weight increased ligand for preparing such a hydrogenation catalyst.

Another object of the present invention is to provide a method for the production of such ligands and catalysts.

Another object of the present invention is to provide a method for asymmetric, homogenous hydrogenation of double bond containing compounds using the catalysts.

These and other objects of the present invention have been satisfied by the discovery of a ligand comprising a molecular weight-enlarged, homogeneously soluble ligand having an average molecular weight in the range from 1,000–1,000,000 g/mol comprising a molecular weight enlarging polymer and one or more ligands, wherein said one or more ligands are homochiral active centers of bis(3,4-diarylphosphinyl)pyrrolidine, wherein said one or more ligands are bound to said molecular weight enlarging polymer via a linker selected from the group consisting of formulae a)–g)

| | | |
|---|---|---|
| a) | —Si(R$_2$)—; | |
| b) | —(SiR$_2$—O)$_n$— | n = 1–10000; |
| c) | —(CHR—CHR—O)$_n$— | n = 1–10000; |
| d) | —(X)$_n$— | n = 1–20; |
| e) | Z—(X)$_n$— | n = 0–20; |
| f) | —(X)$_n$—W | n = 0–20; |
| g) | Z—(X)$_n$—W | n = 0–20; | wherein

R represents H, (C$_1$–C$_8$) alkyl, (C$_6$–C$_{18}$) aryl, (C$_7$–C$_{19}$) aralkyl, or ((C$_1$–C$_8$) alkyl)$_{1-3}$-(C$_6$–C$_{18}$) aryl;

X represents (C$_6$–C$_{18}$) arylene, (C$_1$–C$_8$) alkylene, (C$_1$–C$_8$) alkenylene, ((C$_1$–C$_8$) alkyl)$_{1-3}$-(C$_6$–C$_{18}$) arylene, or (C$_7$–C$_{19}$) aralkylene;

Z represents C(=O)O—, C(=O)NH—, C(=O)—, NR, O, CHR, CH$_2$, C=S, S, PR, wherein Z is further bound directly to said molecular weight enlarging polymer; and W represents C(=O)O—, C(=O)NH—, C(=O)—, NR, O, CHR, CH$_2$, C=S, S, PR, wherein W is further bound directly to said ligand;

or said one or more ligands are bound directly to said molecular weight-enlarging polymer, its use in preparing a catalyst and the catalyst prepared thereby, as well as the use of the catalyst in a method for the production of enantiomerically enriched organic compounds.

DETAILED DESCRIPTION OF THE PREFERRED EMBODIMENTS

The present invention relates to a molecular weight-enlarged, homogeneously soluble ligand having an average molecular weight of 1,000–1,000,000 g/mol which comprises a molecular weight enlarging polymer and one or more ligands, wherein the one or more ligands are homochiral active centers of bis(3,4-diarylphosphinyl)pyrrolidines, wherein these ligands are bound to said polymer via a linker selected from the group consisting of formulae a)–g):

| | | |
|---|---|---|
| a) | —Si(R$_2$)—; | |
| b) | —(SiR$_2$—O)$_n$— | n = 1–10000; |
| c) | —(CHR—CHR—O)$_n$— | n = 1–10000; |
| d) | —(X)$_n$— | n = 1–20; |
| e) | Z—(X)$_n$— | n = 0–20; |
| f) | —(X)$_n$—W | n = 0–20; |
| g) | Z—(X)$_n$—W | n = 0–20; | wherein

R is H, (C$_1$–C$_8$) alkyl, (C$_6$–C$_{18}$) aryl, (C$_7$–C$_{19}$) aralkyl, ((C$_1$–C$_8$) alkyl)$_{1-3}$-(C$_6$–C$_{18}$) aryl, X is (C$_6$–C$_{18}$) arylene, (C$_1$–C$_8$) alkylene, (C$_1$–C$_8$) alkenylene, ((C$_1$–C$_8$) alkyl)$_{1-3}$-(C$_6$–C$_{18}$) arylene, (C$_7$–C$_{19}$) aralkylene, Z represents on the polymer side C(=O)O—, C(=O)NH—, C(=O)—, NR, O, CHR, CH$_2$, C=S, S, PR, W represents on the ligand side C(=O)O—, C(=O)NH—, C(=O)—, NR, O, CHR, CH$_2$, C=S, S, PR, or the active centers are bound directly to the molecular weight-enlarging polymer, and to the polymer-enlarged hydrogenation catalysts formed using these ligands. These catalysts are useful in industrial organic synthesis, and are very readily recyclable.

For the purposes of the present invention, the molecular weight enlarging polymer can be freely selected. The enlargement is limited, on the one hand, by considerations of practicability and cost and, on the other, by technical issues (retention capacity, solubility etc.). Some molecular weight enlarging polymers for catalysts are described in Reetz et al., Angew. Chem. 1997, 109, 1559 et seq.; Seebach et al., Helv. Chim Acta 1996, 79, 1710 et seq.; Kragl et al., Angew. Chem. 1996, 108, 684 et seq.; Schurig et al., Chem. Ber./Recueil 1997, 130, 879 et seq.; Bolm et al., Angew. Chem. 1997, 109, 773 et seq.; Bolm et al. Eur. J. Org. Chem. 1998, 21 et seq.; Baystone et al. in Speciality Chemicals 224 et seq.; Salvadori et al., Tetrahedron: Asymmetry 1998, 9, 1479; Wandrey et al., Tetrahedron: Asymmetry 1997, 8, 1529 et seq.; ibid. 1997, 8, 1975 et seq.; Togni et al. J. Am. Chem. Soc. 1998, 120, 10274 et seq., Salvadori et al., Tetrahedron Lett. 1996, 37, 3375 et seq.; WO 98/22415; and in particular DE 19910691.6, the relevant contents of each of which are hereby incorporated by reference.

Preferred molecular weight-enlarging polymers for binding the ligands are polyacrylates, polyvinylpyrrolidinones, polysiloxanes, polybutadienes, polyisoprenes, polyalkanes, polystyrenes, polyoxazolines or polyethers (PEG, PEP) or mixtures thereof. For the purposes of the present invention, mixtures are taken to mean the fact that individual monomers or polymers of differing origin are polymerised together to yield block copolymers, graft copolymers, random copolymers or even intimate mixtures of two or more polymers (i.e. polymer blends).

Polyacrylates, polystyrenes, polysiloxanes, polyethers and mixtures thereof are particularly preferred for this purpose.

The following structures are extremely preferred, wherein, on a statistical average, the values for a should be 1 and for b 10–30, preferably 20 (scheme 1).

production of a ligand according to the present invention, wherein the process comprises one of the following steps A)–C):

A) binding a ligand having a catalytically active center to a monomer directly or through a linker to provide a ligand modified monomer, then polymerizing said ligand modified monomer in the presence of one or more unmodified monomers;

B) binding a ligand having a catalytically active center to a polymer, either directly or through a linker;

C) following either step A) or B) and further copolymerizing the resulting polymer with one or more additional polymers, wherein said one or more additional polymers optionally comprise one or more catalytically active centers.

The ligand according to the present invention is preferably used for the production of enantiomerically enriched organic compounds. In particular, the present invention further provides a method for the selective production of enantiomerically enriched organic compounds (an enantioselective reaction that generates one enantiomer of a compound selectively over the opposite enantiomer), comprising performing a reaction on a starting material having a non-chiral site, such as a double bond, within the starting material to convert said non-chiral site into a chiral site, wherein said reaction is performed in the presence of a catalyst for said reaction, wherein the catalyst comprises a metal having thereon one or more molecular weight enlarged, homogeneously soluble ligands comprising a molecular weight enlarging polymer and one or more ligands, wherein said one or more ligands are homochiral Scheme 1

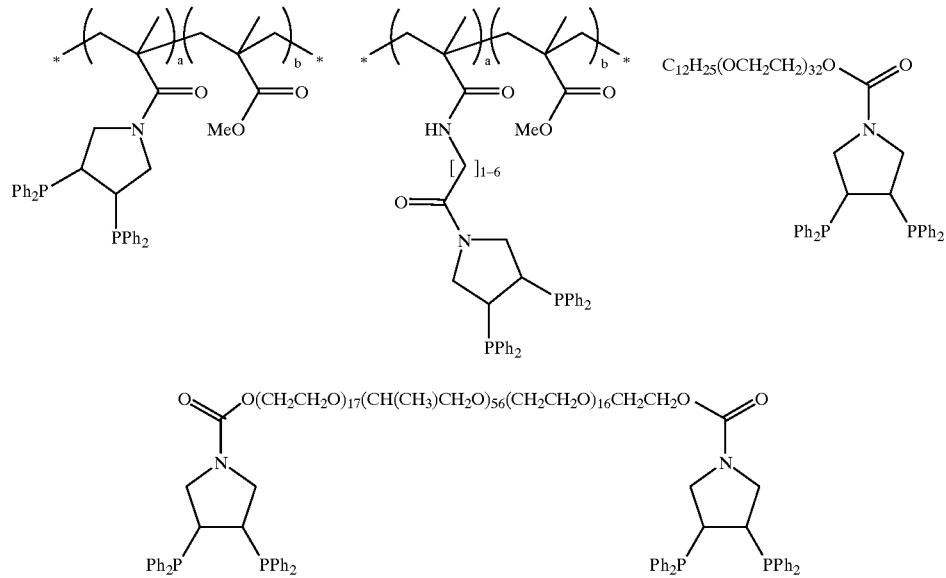

The molecular weight-enlarging polymers preferably exhibit an average molecular weight in the range from 5,000–500,000, particularly preferably from 5,000–300,000 g/mol. The present invention also provides a process for the active centers of bis(3,4-diarylphosphinyl)pyrrolidine, wherein said one or more ligands are bound to said molecular weight enlarging polymer via a linker selected from the group consisting of formulae a)–g)

| | | |
|---|---|---|
| a) | —Si(R$_2$)—; | |
| b) | —(SiR$_2$—O)$_n$— | n = 1–10000; |
| c) | —(CHR—CHR—O)$_n$— | n = 1–10000; |
| d) | —(X)$_n$— | n = 1–20; |
| e) | Z—(X)$_n$— | n = 0–20; |
| f) | —(X)$_n$—W | n = 0–20; |
| g) | Z—(X)$_n$—W | n = 0–20; | wherein

R represents H, (C$_1$–C$_8$) alkyl, (C$_6$–C$_{18}$) aryl, (C$_7$–C$_{19}$) aralkyl, or ((C$_1$–C$_8$) alkyl)$_{1-3}$-(C$_6$–C$_{18}$) aryl;

X represents (C$_6$–C$_{18}$) arylene, (C$_1$–C$_8$) alkylene, (C$_1$–C$_8$) alkenylene, ((C$_1$–C$_8$) alkyl)$_{1-3}$-(C$_6$–C$_{18}$) arylene, or (C$_7$–C$_{19}$) aralkylene;

Z represents C(=O)O—, C(=O)NH—, C(=O)—, NR, O, CHR, CH$_2$, C=S, S, PR, wherein Z is further bound directly to said molecular weight enlarging polymer; and W represents C(=O)O—, C(=O)NH—, C(=O)—, NR, O, CHR, CH$_2$, C=S, S, PR, wherein W is further bound directly to said ligand;

or said one or more ligands are bound directly to said molecular weight-enlarging polymer.

The use thereof in a membrane reactor is particularly preferred. As a result, syntheses normally performed in batch processes may proceed semi-continuously or continuously, which, from a cost standpoint, is particularly advantageous for an industrial process. The ligand according to the present invention, or the catalyst produced therefrom, is used in the membrane reactor in an analogous manner to the process described in DE 199 10 691.6; or Wandrey et al., Tetrahedron Asymmetry 1999, 10, 923–928, the contents of which are incorporated herein by reference.

The hydrogen required for hydrogenation may be supplied to the reactor as a gas. In this case, a semi-continuous processing method is suitable, in which, after hydrogenation in the reactor, the low molecular weight substances are separated and then a new feed batch is introduced and subsequently hydrogenated.

In the case of transfer hydrogenation, however, a continuous processing method is preferred, such as that described in "Asymmetric transfer hydrogenation of C=O and C=N bonds", M. Wills et al. Tetrahedron: Asymmetry 1999, 10, 2045; "Asymmetric transfer hydrogenation catalysed by chiral ruthenium complexes", R. Noyori et al. Acc. Chem. Res. 1997, 30, 97; "Asymmetric catalysis in organic synthesis", R. Noyori, John Wiley & Sons, New York, 1994, S.123; "Transition metals for organic Synthesis", eds. M. Beller, C. Bolm, Wiley-VCH, Weinheim, 1998, vol. 2, p. 97; and "Comprehensive Asymmetric Catalysis", eds.: Jacobsen, E. N.; Pfaltz, A.; Yamamoto, H., Springer-Verlag, 1999, the relevant portions of each of which are hereby incorporated by reference. The membrane reactor may here act as a crossflow or dead end filtration module (DE 19947505.9 and DE 19910691.6 or "Engineering processes for Bioseparations", edited by: Laurence R. Weatherley, pages 135–165; Butterworth-Heinemann, 1994; ISBN: 0 7506 1936 8).

The ligand of the present invention provides a catalyst useful for hydrogenation of compounds containing double bonds, preferably C=C, C=N or C=O double bonds, particularly for selective asymmetric hydrogenation of such compounds.

The present invention also provides a molecular weight-enlarged catalyst comprising a metal or metal ion and one or more molecular weight enlarged ligands, wherein the one or more molecular weight enlarged ligands comprise a molecular weight enlarging polymer and one or more ligands, wherein said one or more ligands are homochiral active centers of bis(3,4-diarylphosphinyl)pyrrolidine, wherein said one or more ligands are bound to said molecular weight enlarging polymer via a linker selected from the group consisting of formulae a)–g)

| | | |
|---|---|---|
| a) | —Si(R$_2$)—; | |
| b) | —(SiR$_2$—O)$_n$— | n = 1–10000; |
| c) | —(CHR—CHR—O)$_n$— | n = 1–10000; |
| d) | —(X)$_n$— | n = 1–20; |
| e) | Z—(X)$_n$— | n = 0–20; |
| f) | —(X)$_n$—W | n = 0–20; |
| g) | Z—(X)$_n$—W | n = 0–20; | wherein

R represents H, (C$_1$–C$_8$) alkyl, (C$_6$–C$_{18}$) aryl, (C$_7$–C$_{19}$) aralkyl, or ((C$_1$–C$_8$) alkyl)$_{1-3}$-(C$_6$–C$_{18}$) aryl;

X represents (C$_6$–C$_{18}$) arylene, (C$_1$–C$_8$) alkylene, (C$_1$–C$_8$) alkenylene, ((C$_1$–C$_8$) alkyl)$_{1-3}$-(C$_6$–C$_{18}$) arylene, or (C$_7$–C$_{19}$) aralkylene;

Z represents C(=O)O—, C(=O)NH—, C(=O)—, NR, O, CHR, CH$_2$, C=S, S, PR, wherein Z is further bound directly to said molecular weight enlarging polymer; and W represents C(=O)O—, C(=O)NH—, C(=O)—, NR, O, CHR, CH$_2$, C=S, S, PR, wherein W is further bound directly to said ligand;

or said one or more ligands are bound directly to said molecular weight-enlarging polymer. In particular, the molecular weight-enlarged catalyst is synthesised from a ligand according to the present invention and a metal or metal ion preferably selected from the group consisting of Ru, Rh, Ir, Pd, Ni, Pt.

Various strategies may be used to synthesize the ligand according to the present invention [such as methods a), b), or c) described above]. How the described linker/active center is bound to the pyrrolidine is left to the discretion of the person skilled in the art, but is preferably achieved by way of the nitrogen function thereof. How the linker/active center is bound to the polymer or monomer is also left to the discretion of the person skilled in the art, but a functionality present on the polymer or monomer is likewise preferably used in this case too. Reactions for achieving this coupling/binding reaction are known to the person skilled in the art.

The basic principle applies that the number of linkers/active centers per monomer in the polymer is as high as possible, such that the conversion rate per mole of polymer is consequently increased. On the other hand, however, the centers should be spaced apart in such a manner that any mutual negative influence on reactivity (TOF, selectivity) is minimized or does not occur. The spacing between linkers/active centers in the polymer should thus preferably be in the range from 5–50 monomer units, preferably 10–25 monomer units.

The site(s) on the polymer or on the monomer to be polymerised which are used for binding the linker/active center are those which may readily be functionalised or permit an existing functionality to be used for binding. Heteroatoms or unsaturated carbon atoms are thus preferably suitable for binding the components.

For example, in the case of styrene/polystyrene, the aromatic rings which are present may be used as attachment points to the linkers/active centers. Functionalities may readily be linked to these aromatic rings, preferably in positions 3, 4, 5, particular preferably in position 4, by means of standard aromatic chemistry, such as electrophilic aromatic acylation or electrophilic aromatic substitution, optionally followed by further functionalization by conventional organic chemistry methods. It is, however, also advantageous to incorporate an already functionalised monomer into the mixture to be polymerised and, after polymerisation, to bind the linker to the functionalities present in the polystyrene. Compounds which are advantageously suitable for this purpose include, for example, para-hydroxy- or para-aminostyrene derivatives.

In the case of polyethers, the existing terminal OH group is suitable for binding to the linkers/active centers by ester or ether formation or by oxidation of this group to form an acid group with subsequent esterification or amide formation (Nagel et al, Chem. Ber. 1986, 119, 3326–3343 hereby incorporated by reference).

In the case of polyacrylates, an acid group or ester group is in each case present in the monomer constituent, to which the linker or the active center may be bound through an ester or amide bond before or after polymerisation.

Polysiloxanes as a molecular weight enlarging polymer are preferably synthesised such that there are intermittent silylene groups modified by alkyl residues comprising double bonds or heteroatoms. The linkers/active centers may then be coupled to these sites.

They may preferably be bound to the functionalities under consideration in the polymer under hydrosilylation conditions (review of the hydrosilylation reaction by Ojima in The Chemistry of Organic Silicon Compounds, 1989 John Wiley & Sons Ltd., 1480–1526 hereby incorporated by reference).

Suitable polysiloxanes modified in this manner are known from the literature ("Siloxane polymers and copolymers" White et al., in S. Patai (ed.), "The Chemistry of Organic Silicon Compounds", Wiley, Chichester, 1989, 46, 2954; C. Wandrey et al. TH:Asymmetry 1997, 8, 1975, relevant portions of these are incorporated by reference).

The purpose of the linker is to provide a space between the active center and the polymer in order to mitigate or eliminate any mutual interactions which are disadvantageous to the reaction. Scheme 2 below provides a suitable overview of linker precursors which may be used to provide a linkage with the polymer/monomer and active center.

Scheme 2

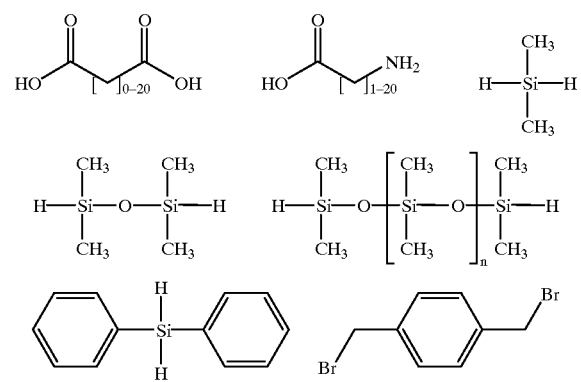

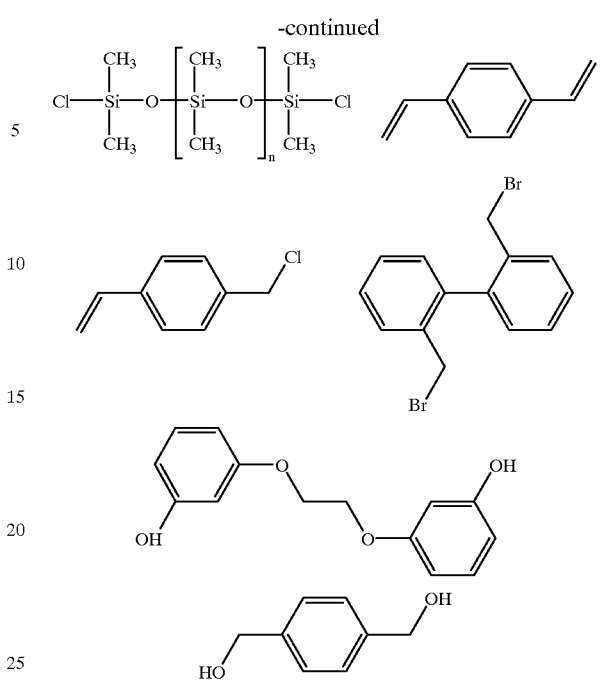

Selection is made on the basis of the possibility of readily coupling the linker, on the one hand, to the active center and, on the other, to the polymer/monomer. Preferred linkers, however, are those such as, for example, 1,4'-biphenyl, 1,2-ethylene, 1,3-propylene, PEG (2–10), α,ω-siloxanylene or 1,4-phenylene and α,ω-1,4-bisethylenebenzene or linkers which are obtainable from siloxanes of the general formula I:

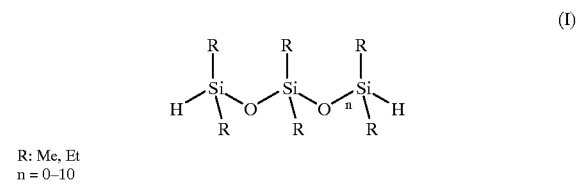

R: Me, Et
n = 0–10

These may be bound to any double bonds present in the polymers and suitable functional groups of the active centre under hydrosilylation conditions. Linkers based on amino acids or dicarboxylic acids are most preferred.

For the purposes of the present invention, active center means the monomeric ligand bis(3,4-diarylphosphinyl) pyrrolidines. The word aryl means in this connection $(C_6-C_{18})$ aryl groups and $((C_1-C_8)$ alkyl$)_{1-3}$-$(C_6-C_{18})$ aryl groups.

$(C_1-C_8)$ Alkyl should be taken to include methyl, ethyl, n-propyl, isopropyl, n-butyl, isobutyl, sec-butyl, tert-butyl, pentyl, hexyl, heptyl or octyl, including all bond isomers. In this connection, a $(C_1-C_8)$ alkoxy residue is a $(C_1-C_8)$ alkyl residue, which is bound via an oxygen atom to the molecule concerned.

$(C_1-C_8)$ alkenylene means a $(C_1-C_8)$ alkylene, with the proviso that at least one double bond is present in the residue.

A $(C_6-C_{18})$ aryl residue is taken to mean an aromatic residue having 6 to 18 C atoms. These in particular include compounds such as phenyl, naphthyl, anthryl, phenanthryl, or biphenyl residues. This residue may be substituted with one or more groups such as $(C_1-C_8)$ alkoxy, $NR_2$, or $(C_1-C_8)$ haloalkyl, such as $CF_3$.

A ($C_7$–$C_{26}$) aralkyl residue is a ($C_6$–$C_{18}$) aryl residue bound to the molecule via a ($C_1$–$C_8$) alkyl residue.

A ($C_7$–$C_{26}$) aralkylene residue should be taken to mean a residue which is attached to the molecule, on the one hand, via the ($C_1$–$C_8$) alkyl residue and, on the other, via the ($C_6$–$C_{18}$) aryl residue.

For the purposes of the present invention, a membrane reactor is taken to mean any reaction vessel in which the catalyst is enclosed in a reactor, while low molecular weight substances are supplied to the reactor or are able to leave it. The membrane can be incorporated directly into the reaction chamber or can be installed in a separate filtration module, in which the reaction solution flows continuously or intermittently through the filtration module and the retentate is returned to the reactor. Suitable embodiments are described, inter alia, in WO98/22415 and in Wandrey et al. in Jahrbuch 1998, Verfahrenstechnik und Chemieingenieurwesen, VDI pp. 151 et seq.; Wandrey et al. in Applied Homogeneous Catalysis with Organometallic Compounds, Vol. 2, VCH 1996, pp. 832 et seq.; Kragl et al., Angew. Chem. 1996, 6, 684 et seq., the relevant portions of each of which are incorporated herein by reference.

Having generally described this invention, a further understanding can be obtained by reference to certain specific examples which are provided herein for purposes of illustration only and are not intended to be limiting unless otherwise specified.

EXAMPLES

Acylation to Yield MMA-PYRPHOS (3,4-bis (diphenylphosphino)-N-isobutenonepyrrolidine)

1.54 g of methacryloyl chloride in 35 mL of toluene were slowly added dropwise at 0° C. to a solution of 5.00 g of 3,4-bis(diphenylphosphino)pyrrolidine in 20 mL of toluene and 20 mL of 2N NaOH. Once the reaction was complete, the phases were separated and the aqueous phase extracted with toluene. The combined organic phases were washed in succession with dilute hydrochloric acid and saturated NaCl solution. After drying over magnesium sulfate, the solvent was stripped out under a vacuum. 5.7 g of the desired product were obtained as a white powder. NMR analysis confirmed the identity of the desired product.

Polymerisation to Yield PMMA-PYRPHOS 20.0 mmol of methyl methacrylate (MMA) and 0.1 mmol of azoisobutyronitrile (AIBN) were added to a solution of 1.0 mmol of MMA-Pyrphos in methyl isobutyl ketone. After heating to 80° C. over 20 h, the product was precipitated in petroleum ether and filtered out. 1.5 g of the desired polymer were obtained as a white powder. NMR analysis confirmed the identity of the desired product.

Asymmetric Hydrogenation

A solution of 182 mg of PMMA-Pyrphos and 2.00 g of acetamidocinnamic acid in 60 mL of MeOH/$H_2O$ (5:1) was stirred at 50° C. and 50 bar $H_2$ until no further hydrogen was absorbed.

The pressure vessel was then depressurised and the reaction solution extracted with ether. After drying the organic phase over magnesium sulfate, the solvent was stripped out under a vacuum. 1.8 g of N-Ac-phenylalanine were obtained with selectivity of ee=40%. HPLC analysis confirmed the identity of the desired product.

Production of Polyether-Pyrphos

1. Chloroformic acid esters

All operations were performed under argon in order to exclude air and moisture.

A solution of 1.32 g (1.1 mmol) of Brij 35 ($C_{12}H_{25}$ ($OCH_2CH_2)_{32}OH$) or of 5.24 g (1;1[sic] mmol) of Synperonic PE/P 103 ($HO(CH_2CH_2O)_{17}(CH(CH_3)CH_2O)_{56}$ ($CH_2CH_2O)_{17}H$) in 10 ml of dichloromethane was slowly added dropwise to 90 ml of a solution of phosgene (1.7662 mmol/ml) cooled to −40° C. and adjusted to 0° C. within 5 h. The excess phosgene was removed with appropriate safety precautions by concentrating the solution to approx. 3 ml and the remaining residue was directly further used.

2. Reaction of the chloroformic acid esters with pyrphos ((R,R)-3,4-bis(diphenylphosphino)pyrrolidine)

1.1 mmol of the corresponding chloroformic acid ester in 3 ml of $CH_2Cl_2$ were added under an argon atmosphere and with stirring at 0° C. to a solution of 0.483 g (1.1 mmol) of Pyrphos and 0.18 ml (1.32 mmol) of triethylamine in 10 ml of dichloromethane. The reaction mixture was stirred for three hours at 0 to 5° C. and then concentrated. The residue was redissolved in 10 ml of ether and left to stand overnight to crystallise the triethylamine hydrochloride. On the next day, the mixture was inert-filtered, the filtrate concentrated and the residue dried under a vacuum at 50° C.

Analysis of the derivative (I) derived from Brij 35: $C_{87}H_{143}NO_{25}P_2$ (1664.82)

Calc.: C=62.76%; H=8.65%; N=0.84%; P=3.72%

Found: C=63.57%; H=8.48%; N=1.26%; P=4.11%

$^{31}P$=−11.8 ppm ($CDCl_3$) Yield=1.34 g (80.5%)

Analysis of derivative (II) derived from the block copolymer Synperonic PE/P 103: $C_{294}H_{524}N_2O_{94}P_4$ (5714.51)

Calc.: C=61.96%; H=9.27%; N=0.49%; P=2.17%

Found: C=62.13%; H=9.15%; N=0.91%; P=2.48%

$^{31}P$=−11.8 ppm ($CDCl_3$) Yield=5.27 g (92.2%)

Hydrogenation of (Z)-α-acetamidocinnamic acid methyl ester in water and methanol with the catalyst system: [$Rh(COD)_2$]$BF_4$ + amphiphilised ligands (I) and (II); $H_2$ 1 bar; 25° C.

| Medium | Rh:I:substrate | t ½ (min) | % eeS | Conversion, % |
|---|---|---|---|---|
| $H_2O$ | 1:1:100 | ~10 h | 88 | 98 (Rh° ↓) |
| | Rh:II:substrate | | | |
| $H_2O$ | 2:1:100 | ~12 h | 80 | 94 (Rh° ↓) |
| $H_2O$ | 1:0.5:100 | ~11 h | 83 | 96 (Rh° ↓) |
| Methanol | 1:0.5:100 | 248 min | 88 | 100 |
| $H_2O$ + SDS (Rh: SDS = 1:2) | 1:0.5:100 | ~9 h | 79 | 97 |

SDS: sodium dodecyl sulfate

In a new batch, 1 mmol of substrate, 0.0005 mmol of ligand (II), 0.001 mmol of $Rh(COD)_2BF_4$ were dissolved in 15 ml of methanol. Hydrogenation was performed in the first case at 10 bar, RT and 24 h, and in the second case at 20 bar, RT and 24 h.

Result: case 1) 88.6% ee; case 2) 89.5% ee

The term "ee" refers to the conventional term "enantiomeric excess" defined as:

Enantiomeric excess of isomer 1=% isomer 1−% isomer 2; wherein % isomer 1+% isomer 2=100%.

Accordingly a reaction that results in 95% isomer 1 and 5% isomer 2 would have an ee of isomer 1=90% ee.

The present application is based on German Patent Application 100 02 973.6, filed in the German Patent Office on Jan. 24, 2001, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

What is claimed is:

1. A ligand, comprising:
a molecular weight-enlarged, homogeneously soluble ligand which comprises:
  a molecular weight enlarging polymer; and
  one or more ligands;
wherein said one or more ligands are homochiral active centers of bis(3,4-diarylphosphinyl)pyrrolidine;
wherein said one or more ligands are bound to said molecular weight enlarging polymer via a linker selected from the group consisting of formulae a)–g)
  a) —Si($R_2$)—;
  b) —(Si$R_2$—O)$_n$—, wherein n=1–10000;
  c) —(CHR—CHR—O)$_n$—, wherein n=1–10000;
  d) —(X)$_n$—, wherein n=1–20;
  e) Z—(X)$_n$—, wherein n=0–20;
  f) —(X)$_n$—W, wherein n=0–20;
  g) Z—(X)$_n$—W, wherein n=0–20; wherein
    R represents H, ($C_1$–$C_8$) alkyl, ($C_6$–$C_{18}$) aryl, ($C_7$–$C_{19}$) aralkyl, or (($C_1$–$C_8$) alkyl)$_{1-3}$-($C_6$–$C_{18}$) aryl;
    X represents ($C_6$–$C_{18}$) arylene, ($C_1$–$C_8$) alkylene, ($C_1$–$C_8$) alkenylene, (($C_1$–$C_8$) alkyl)$_{1-3}$-($C_6$–$C_{18}$) arylene, or ($C_7$–$C_{19}$) aralkylene;
    Z represents C(=O)O—, C(=O)NH—, C(=O)—, NR, O, CHR, $CH_2$, C=S, S or PR, wherein Z is further bound directly to said molecular weight enlarging polymer; and
    W represents C(=O)O—, C(=O)NH—, C(=O)—, NR, O, CHR, $CH_2$, C=S, S or PR, wherein W is further bound directly to said ligand;
    or said one or more ligands are bound directly to said molecular weight-enlarging polymer;
wherein the molecular weight enlarging polymer is a member selected from the group consisting of polyacrylates, polyvinylpyrrolidinones, polysiloxanes, polybutadienes, polyisoprenes, polyalkanes, polystyrenes, polyoxazolines and mixtures thereof.

2. A method for the production of a molecular weight enlarged ligand, comprising:
a step selected from the group consisting of steps A)–C):
  A) binding a ligand having a catalytically active center to a monomer directly or through a linker to provide a ligand modified monomer, then polymerizing said ligand modified monomer in the presence of one or more unmodified monomers, to obtain a polymer;
  B) binding a ligand having a catalytically active center to a polymer, either directly or through a linker, to obtain a polymer;
  C) following either steps A) or B), further copolymerizing said polymer with one or more additional polymers, wherein said one or more additional polymers optionally comprise one or more catalytically active centers;
wherein said molecular weight enlarged ligand comprises a molecular weight enlarging polymer which is selected from the group consisting of polyacrylates, polyvinylpyrrolidinones, polysiloxanes, polybutadienes, polyisoprenes, polyalkanes, polystyrenes, polyoxazolines and mixtures thereof;
wherein said linker of steps A) and B) is a member selected from the group consisting of formulae a)–g)
  a) —Si($R_2$)—;
  b) —(Si$R_2$—O)$_n$—, wherein n=1–10000;
  c) —(CHR—CHR—O)$_n$—, wherein n=1–10000;
  d) —(X)$_n$—, wherein n=1–20;
  e) Z—(X)$_n$—, wherein n=0–20;
  f) —(X)$_n$—W, wherein n=0–20;
  g) Z—(X)$_n$—W, wherein n=0–20; wherein
    R represents H, ($C_1$–$C_8$) alkyl, ($C_6$–$C_{18}$) aryl, ($C_7$–$C_{19}$) aralkyl, or (($C_1$–$C_8$) alkyl)$_{1-3}$-($C_6$–$C_{18}$) aryl;
    X represents ($C_6$–$C_{18}$) arylene, ($C_1$–$C_8$) alkylene, ($C_1$–$C_8$) alkenylene, (($C_1$–$C_8$) alkyl)$_{1-3}$-($C_6$–$C_{18}$) arylene, or ($C_7$–$C_{19}$) aralkylene;
    Z represents C(=O)O—, C(=O)NH—, C(=O)—, NR, O, CHR, $CH_2$, C=S, S or PR, wherein Z is further bound directly to said molecular weight enlarging polymer; and
    W represents C(=O)O—, C(=O)NH—, C(=O)—, NR, O, CHR, $CH_2$, C=S, S or PR, wherein W is further bound directly to said ligand.

3. The method of claim 2, wherein said ligand of steps A) and B) comprises a homochiral active center of bis(3,4-diarylphosphinyl)pyrrolidine.

4. The method according to claim 2, wherein the molecular weight enlarged ligand is homogeneously soluble.

5. A method for the selective production of enantiomerically enriched organic compounds, comprising:
reacting a starting material having a non-chiral site within the starting material to convert said non-chiral site into a chiral site;
wherein said reacting is performed in the presence of a catalyst;
wherein said catalyst comprises a metal having thereon one or more molecular weight enlarged, homogeneously soluble ligands comprising:
  a molecular weight enlarging polymer; and
  one or more ligands;
wherein said one or more ligands are homochiral active centers of bis (3,4-diarylphosphinyl)pyrrolidine;
wherein said one or more ligands are bound to said molecular weight enlarging polymer via a linker selected from the group consisting of formulae a)–g)
  a) —Si($R_2$)—;
  b) —(Si$R_2$—O)$_n$—, wherein n=1–10000;
  c) —(CHR—CHR—O)$_n$—, wherein n=1–10000;
  d) —(X)$_n$—, wherein n=1–20;
  e) Z—(X)$_n$—, wherein n=0–20;
  f) —(X)$_n$—W, wherein n=0–20;
  g) Z—(X)$_n$—W, wherein n=0–20; wherein
    R represents H, ($C_1$–$C_8$) alkyl, ($C_6$–$C_{18}$) aryl, ($C_7$–$C_{19}$) aralkyl, or (($C_1$–$C_8$) alkyl)$_{1-3}$-($C_6$–$C_{18}$) aryl;
    X represents ($C_6$–$C_{18}$) arylene, ($C_1$–$C_8$) alkylene, ($C_1$–$C_8$) alkenylene, (($C_1$–$C_8$)alkyl)$_{1-3}$-($C_6$–$C_{18}$) arylene, or ($C_7$–$C_{19}$) aralkylene;
    Z represents C(=O)O—, C(=O)NH—, C(=O)—, NR, O, CHR, $CH_2$, C=S, S or PR, wherein Z is further bound directly to said molecular weight enlarging polymer; and
    W represents C(=O)O—, C(=O)NH—, C(=O)—, NR, O, CHR, $CH_2$, C=S, S or PR, wherein W is further bound directly to said ligand;
    or said one or more ligands are bound directly to said molecular weight-enlarging polymer;
wherein the molecular weight enlarging polymer is a member selected from the group consisting of polyacrylates, polyvinylpyrrolidinones, polysiloxanes, polybutadienes, polyisoprenes, polyalkanes, polystyrenes, polyoxazolines and mixtures thereof.

6. The method of claim 5, wherein said reacting is performed in a membrane reactor.

7. The method of claim 5, wherein said reacting is hydrogenating of one or more C=C, C=N or C=O double bonds in the starting material.

8. The method of claim 7, wherein said hydrogenating is transfer hydrogenating.

9. A molecular weight-enlarged catalyst, comprising:
a metal or metal ion; and
one or more molecular weight enlarged ligands;
wherein the one or more molecular weight enlarged ligands comprise:
a molecular weight enlarging polymer; and
one or more ligands;
wherein said one or more ligands are homochiral active center of bis (3,4-diarylphosphinyl)pyrrolidine;
wherein said one or more ligands are bound to said molecular weight enlarging polymer via a linker selected from the group consisting of formulae a)–g)
a) —Si($R_2$)—;
b) —(Si$R_2$—O)$_n$—, wherein n=1–10000;
c) —(CHR—CHR—O)$_n$—, wherein n=1–10000;
d) —(X)$_n$—, wherein n=1–20;
e) Z—(X)$_n$—, wherein n=0–20;
f) —(X)$_n$—W, wherein n=0–20;
g) Z—(X)$_n$—W, wherein n=0–20; wherein R represents H, ($C_1$–$C_8$) alkyl, ($C_6$–$C_{18}$) aryl, ($C_7$–$C_{19}$) aralkyl, or (($C_1$–$C_8$) alkyl)$_{1-3}$-($C_6$–$C_{18}$) aryl;

X represents ($C_6$–$C_{18}$) arylene, ($C_1$–$C_8$) alkylene, ($C_1$–$C_8$) alkenylene, (($C_1$–$C_8$) alkyl)$_{1-3}$-($C_6$–$C_{18}$) arylene, or ($C_7$–$C_{19}$) aralkylene;

Z represents C(=O)O—, C(=O)NH—, C(=O)—, NR, O, CHR, $CH_2$, C=S, S or PR, wherein Z is further bound directly to said molecular weight enlarging polymer; and W represents C(=O)O—, C(=O)NH—, C(=O)—, NR, O, CHR, $CH_2$, C=S, S or PR, wherein W is further bound directly to said ligand;

or said one or more ligands are bound directly to said molecular weight-enlarging polymer;

wherein the molecular weight enlarging polymer is a member selected from the group consisting of polyacrylates, polyvinylpyrrolidinones, polysiloxanes, polybutadienes, polyisoprenes, polyalkanes, polystyrenes, polyoxazolines and mixtures thereof.

10. The molecular weight enlarged catalyst according to claim 9, wherein said metal is selected from the group consisting Ru, Rh, Ir, Pd, Ni and Pt; and wherein said metal ion is selected from the group consisting of a Ru ion, a Rh ion, an Ir ion, a Pd ion, a Ni ion and a Pt ion.

* * * * *